United States Patent

Ogoshi et al.

[11] 4,036,596
[45] July 19, 1977

[54] APPARATUS FOR CONTINUOUS SULFONATION

[75] Inventors: Toshiaki Ogoshi, Funabashi; Yozo Miyawaki; Fusao Kondo, both of Chiba; Susumu Sakurai, Narashino, all of Japan

[73] Assignee: Lion Fat & Oil Co., Ltd., Tokyo, Japan

[21] Appl. No.: 699,712

[22] Filed: June 25, 1976

[30] Foreign Application Priority Data

June 30, 1975 Japan .................... 50-80645

[51] Int. Cl.² ............ B01J 10/00; C07B 13/06
[52] U.S. Cl. ............................ 23/283; 261/112
[58] Field of Search ........... 23/284, 285, 283, 266; 260/458, 459 R, 513 T, 505 R; 261/112

[56] References Cited

U.S. PATENT DOCUMENTS

| | | |
|---|---|---|
| 3,328,460 | 6/1967 | Vander Mey ............ 260/458 X |
| 3,879,172 | 4/1975 | Toyoda et al. ............ 23/284 |
| 3,918,917 | 11/1975 | Ashina et al. .......... 260/458 R X |

Primary Examiner—Morris O. Wolk
Assistant Examiner—Roger F. Phillips
Attorney, Agent, or Firm—Bacon & Thomas

[57] ABSTRACT

A cylindrical apparatus for continuous sulfonation of an organic liquid is provided with an annular feeding device for permitting the organic liquid to flow in the form of a film down a reaction wall. The annular feeding device is provided with a number of slots in a horizontal and equidistant manner in a row.

6 Claims, 3 Drawing Figures

APPARATUS FOR CONTINUOUS SULFONATION

This invention relates to an apparatus for continuous sulfonation of an organic liquid. More particularly, this invention relates to an improved apparatus for continuously sulfonating the organic liquid by permitting it to flow in the form of a film down a reaction wall to undergo a gas-liquid contact reaction with sulfur trioxide. The term "sulfonation" hereinafter used in the specification and in the claims is defined to means both the sulfonation and the sulfation.

A surface-active agent such as alkylbenzene sulfonate, alkyl sulfate, or α-olefin sulfonate is produced by utilizing the sulfonation reaction. In the production of, for example, alkyl sulfate, the sulfonation is performed wherein a sulfur trioxide (having a $SO_3$ concentration of 2 to 8%) diluted by air or an inert gas such as nitrogen gas is allowed to contact a liquid raw material. Such sulfonation based on the use of sulfur trioxide is not limited to the above example but is widely utilized for the production of surface-active agent or dyes.

The above-mentioned sulfonation, however, is a rapid exothermic reaction. Upon the gas-liquid contact reaction with sulfur trioxide, the film thickness, or the flow quantity, of the organic liquid to be sulfonated has to be maintained uniform. Otherwise, the resulting final product is too coloured. In a conventional sulfonation apparatus, however, difficulties were encountered in maintaining the film thickness or the quality of the organic liquid, for which reason the quality of the resulting final product failed to be satisfactory.

As a result of having conducted detailed studies on the reason why the final product obtained by the conventional sulfonation apparatus was coloured, it has been determined that there exist various reasons or causes including the following.

The conventional sulfonation apparatus is generally so constructed that an organic liquid is allowed to flow in the form of a thin film down two externally cooled, substantially concentric, circular reaction surfaces from a circular slit opening located on an upper part of said reaction surfaces, and is allowed to contact the sulfur trioxide introduced in parallel-flow relation to the organic liquid. A typical example thereof is disclosed in detail, for example, in U.S. Pat. No. 3,620,684. The organic liquid-feeding opening used in the above-mentioned conventional sulfonation apparatus is of a horizontally circular slit shape and has no vertical partition. By adjusting the vertical clearance of the slit, the film thickness or flow quantity of the organic liquid is so controlled as to be made uniform at all points of the reaction surface. Since, however, the circular slit opening has as large a diameter as, for example, 500 mm to 600 mm, even a small error in terms of the vertical clearance of slit results in a large difference in terms of film thickness between both ends of the slit diameter. For example, even such a small error as ±0.01 mm results in about 10% of error in terms of flow quantity.

In order to remove the foregoing drawbacks to prevent a final product from being coloured, several improvements have thereafter been proposed. For example, U.S. Pat. No. 3,677,714 discloses the formation of a uniform film of organic liquid on the reaction surface by providing a porous substance for the organic liquid-feeding opening, while U.S. Pat. No. 3,879,172 discloses the same formation by providing a net for the organic liquid-feeding opening. But, when it is desired to form, in such cases, a uniform film of organic liquid over an entire area of circular reaction surface, some pressure loss is required to exist between the pressure at the front of the porous substance or net and that at the back thereof. Accordingly, the pore size of the porous substance or the mesh size of the net is made small. This is apt to cause the occurrence of clogging. Therefore the film thickness of the organic liquid becomes likely to be non-uniform. With the passage of operation time, therefore, a sulfonation product comes to be coloured, so that a long-time operation is difficult.

Accordingly, an object of the invention is to provide an apparatus for continuous sulfonation eliminating the above-mentioned drawbacks of the conventional sulfonation apparatus to produce a final product of high quality.

Another object of the invention is to provide an apparatus for continuous sulfonation with a feeding device, which enables the formation of a uniform thin film of organic liquid.

The apparatus for continuously sulfonating an organic liquid by the use of a gaseous sulfonating agent in accordance with the object of the invention is constructed such that, for the purpose of permitting the organic liquid to be sulfonated to flow in the form of a thin film down a vertically extending, cylindrical reaction surface, an annular feeding device having a number of slots horizontally equidistantly arranged in a row is provided at an upper end of the cylindrical reaction wall. As for this annular feeding device, the vertical clearance $a$ of opening of such slot, the interval $b$ between adjacent two of the slots and the horizontal width $c$ of opening of each slot are so selectively determined that the percentage of slot area exposed by the formula:

$$\frac{a \times c}{a(b + c)} \times 100$$

ranges from 40% to 90%.

This invention can be more fully understood from the following detailed description when taken in conjunction with the accompanying drawings, in which.

Figure 1:
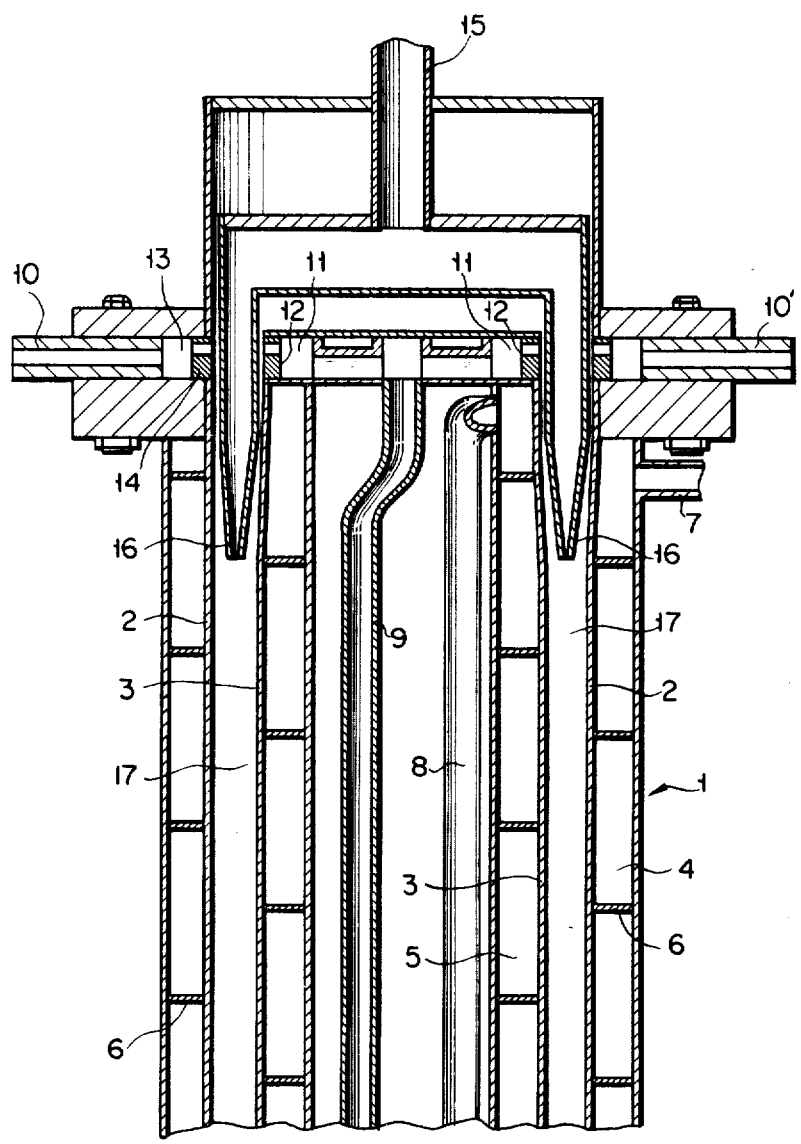
FIG. 1 is a vertical sectional view of an example of an apparatus for continuous sulfonation according to the invention.

The above-mentioned annular feeding device for feeding organic liquid is provided at the upper end of a cylindrical reaction wall. Slightly below the annular feeding device is opened an annular nozzle for feeding sulfur trioxide in parallel-flow relation to a downflow film of the organic liquid.

In the annular feeding device of the invention, the vertical clearance $a$ of opening of each slot is preferably in the range of 0.2 mm to 1.0 mm. Where the $a$ is smaller than 0.2 mm, the slot becomes likely to be subject to clogging and the manufacturing precision is not sufficiently increased. In contrast, where the $a$ exceeds 1.0 mm, the pressure loss is decreased to make the flow quantity nonuniform, thereby to undesirably influence the sulfonation reaction.

The interval $b$ between adjacent two of the slots is preferably in the range of 1 mm to 5 mm. Where the $b$ exceeds 5 mm, the cylindrical reaction surface comes to have the portions which fail to be covered with the organic liquid, so that the resulting final product is coloured. In contrast, where the $b$ is smaller than 1 mm, difficulties are encountered in manufacturing the apparatus although no undesirable effect acts on the formation of a uniform thin film of the organic liquid.

Preferably, the slot is of a rectangular shape. But this invention is not limited thereto and includes a slot both upper angles of whose rectangular shape are round, a semicircular slot, etc. Those skilled in the art would be able to easily apply this invention to these slots.

The percentage of area of the slots provided, as above described, in the annular feeding device in a row and in a horizontal and equidistant manner is in the range of 40 to 90%, or preferably 50 to 90%. This percentage of slot area is expressed as follows.

$$\frac{a \times c}{a(b + c)} \times 100$$

where $a$ represents the vertical clearance of opening of the slot, $b$ the interval between adjacent two of the slots, and $c$ the horizontal width of the slot.

Where the percentage of slot area is less than 40%, it is difficult to form a uniform thin film of organic liquid on the cylindrical reaction surface.

On the contrary, where the percentage of slot area exceeds 90%, small errors in terms of the vertical clearance of the slot remarkably influence the quantity of flow and the pressure loss becomes extremely small. As a result, a uniform thin film of organic liquid is not obtained. In order to form a stable uniform film of organic liquid by using the annular feeding device of the invention, pressure loss is always needed.

The quality of material of which the annular feeding device of the invention is formed has to be inactive against the organic liquid to be sulfonated and preferably includes stainless steel, bronze, plastic material, etc.

The apparatus for continuous sulfonation according to the invention can be widely used for sulfonation of the organic liquid by sulfur trioxide, and is more preferably used for sulfonation of alkylbenzene having an alkyl group having eight to 15 carbon atoms, olefinic hydrocarbons having 10 to 24 carbon atoms such as α-olefin, inner-olefin or vinylidene type olefin, aliphatic alcohol having nine to 16 carbon atoms, alkylphenol having alkyl group having six to 14 carbon atoms added with 1 to 10 mols of ethylene oxide, aliphatic alcohol having nine to 19 carbon atoms added with 1 to 10 mols of ethylene oxide, or lower ($C_1$ to $C_4$) alcohol ester of fatty acid having eight to 20 carbon atoms. Besides, aromatic hydrocarbon such as benzene, toluene or xylene can also be used as the organic liquid to be sulfonated.

The above-mentioned organic liquids to be sulfonatedare fed to the apparatus for continuous sulfonation at the rate of 50 to 500 kg/m.hr (the weight of the organic liquid flowing per hour and per meter of the circumferential length of the cylindrical reaction surface). In the apparatus for continuous sulfonation, the molar ratio of $SO_3$ as a sulfonating agent to the organic liquid to be sulfonated is preferably in the range of 0.90 to 1.30. The $SO_3$ to be fed is usually diluted by air or an inert gas such as nitrogen gas so as to account for 1 to 12% by volume of a total amount of the resulting gas, and the flow rate of the $SO_3$ gas when it contacts the organic liquid is preferably in the range of 20 to 100 m/sec.

The above sulfonation is an exothermic reaction, and sometimes the temperature of the reaction product immediately after the commencement of the reaction is raised up to nearly 100° C. In order to suppress such temperature elevation and maintain the reaction temperature at about 30° C to 80° C, the reaction wall is provided with a cooling jacket to be cooled by water or cooling medium. Subsequently, the sulfonated organic liquid such as alkylbenzene is neutralized by, for example, caustic alkali or organic base, whereby a surface-active agent is produced.

In FIG. 1 showing an example of the apparatus for continuous sulfonation according to the invention, the apparatus 1 is substantially cylindrical and is constructed such that two externally cooled cylindrical reaction walls, namely an outer reaction wall 2 and an inner reaction wall 3, are vertically and concentrically disposed with their respective reaction surfaces opposed to each other. The cylindrical reaction walls 2, 3 are provided with cooling jackets 4, 5 respectively, and for removing the reaction heat the water or cooling medium is fed from the bottoms of the jackets and is allowed to rise while being revolved by baffle plates 6 and is discharged to the exterior from cooling water discharge pipes 7, 8 respectively.

The organic liquid to be sulfonated such as α-olefin having 10 to 24 carbon atoms is introduced from an inner raw material feed pipe 9 and outer raw material feed pipes 10, 10'. The organic liquid introduced from the inner raw material feed pipe 9 flows in the form of a thin film down the reaction surface of the inner reaction wall 3 from an inner annular feeding device 12 through a circular chamber 11. Similarly, the organic liquid introduced from the outer raw material feed pipes 10, 10' flows in the form of a thin film down the reaction surface of the outer reaction wall 2 from an outer annular feeding device 14 through a circular chamber 13.

The sulfur trioxide as a gaseous sulfonating agent is fed from a $SO_3$ gas feeding pipe 15 and is introduced into a reaction zone 17 from an annular $SO_3$-feeding nozzle 16 inserted between the two reaction walls 2, 3. Preferably the opening position of the annular $SO_3$-feeding nozzle 16 is situated slightly below the annular feeding devices 12, 14. The $SO_3$ gas introduced into the reaction zone 17 acts on a thin film of organic liquid from immediately below the nozzle 16 to sulfonate it. While the organic liquid is flowing down the reaction surfaces, said sulfonation is completed. The sulfonated organic liquid is taken out from a product take-out pipe (not shown) provided below the reaction zone 17.

Figure 3:
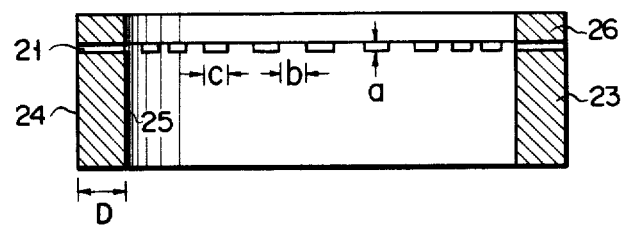
FIG. 3 is a vertical sectional view taken along line X-X' of FIG. 2.
Figure 2:
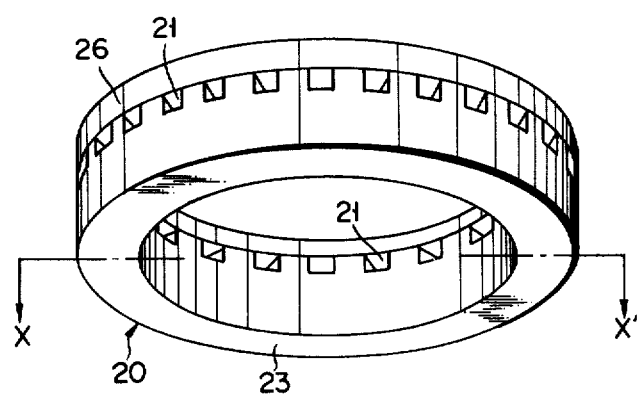
FIG. 2 is a perspective view of an annular feeding device for feeding organic liquid according to the invention.

FIG. 2 is a perspective view of an annular feeding device according to the invention. FIG. 3 is a longitudinal sectional view taken along the line X-X' of FIG. 2. As shown, an annular feeding device 20 has a number of slots 21 provided in a row in a horizontal and equidistant manner. Preferably, the thickness D of an annular wall 23 of the annular feeding device 20 is in the range of about 3 mm to 15 mm. As seen from FIG. 3, the slots 21 are provided through the annular wall 23. Where the annular feeding device 20 is the above-mentioned inner feeding device, an organic liquid to be sulfonated is fed to the inside of this device and is passed through the slots 21 to flow in the form of a thin film down the outer surface 24 of the device and further flow down the reaction surface of the inner reaction wall 3 so provided that its surface is in alignment with the outer surface 24.

Where the annular feeding device 20 is the above-mentioned outer feeding device, the organic liquid is fed to the outside of this device and is passed through the slots 21 to flow down the inner surface 25.

In FIG. 3, $a$ represents the vertical clearance of the opening of each slot, $b$ the interval between adjacent two of the slots, and $c$ the horizontal width of the opening of each slot.

The annular feeding device 20 according to the invention is prepared by subjecting one end of the annular wall 23 to precision fabrication into a comb-like configuration and connection an annular member 26 with said one end thus formed. Upon horizontally installing the annular feeding device on the apparatus for continuous sulfonation, said contact-bonding may be effected, for example, by bolts. In the case of the inner annular feeding device, a circular plate can also be used for the annular member 26. The annular feeding devices are used in the same number as that of the reaction walls, and generally two annular feeding devices are used per apparatus for continuous sulfonation.

eight positions of the inner reaction surface (76 mm in diameter) corresponding to those of the outer surface of the inner annular feeding device which were respectively vertically downwardly spaced 5 cm from the eight positions obtained by dividing said outer surface of the device into eight equal parts. The error of the flow quantity from which the uniformity of the resulting thin film is determined is calculated by the following equation.

$$\text{Error of flow quantity} = \frac{\text{Flow quantity at respective measuring positions}}{\text{Average value of flow quantity at respective measuring positions}} \times 100 - 100$$

The organic liquid used was α-olefin having 16 to 18 carbon atoms (having an average molecular weight of 235). The configuration of the annular feeding devices used and the results of measurement are presented in Table 1 below.

Table 1

| Annular feeding device | Apparatus for continuous sulfonation provided with annular feeding devices | | | | | | | Prior art |
|---|---|---|---|---|---|---|---|---|
| a (mm) | 0.4 | 0.4 | 0.4 | 0.4 | 0.4 | 0.4 | 0.4 | 0.3 (slit) |
| b (mm) | 3 | 3 | 3 | 3 | 3 | 3 | 3 | |
| Percent of slot area (%) | 35 | 40 | 50 | 67 | 80 | 90 | 95 | 100 |
| Pressure drop Δp(mm H₂O) | 48 | 46 | 44 | 32 | 22 | 19 | 17 | 37 |
| Errors of flow quantity at respective measuring positions | | | | | | | | |
| Measuring position 1 | +1.5 | +0.5 | +0.2 | 0 | −0.7 | −0.5 | +2.1 | +25.5 |
| " 2 | +2.6 | +0.7 | +0.1 | −0.1 | 0 | −0.3 | −0.6 | −5.2 |
| " 3 | −3.2 | −2.5 | 0 | +1.7 | +1.5 | 0 | −2.5 | −2.5 |
| " 4 | −2.9 | −1.7 | −2.1 | +1.0 | −0.9 | +2.5 | −2.6 | +10.3 |
| " 5 | +3.8 | +2.6 | +1.5 | −1.6 | −0.1 | +2.1 | −2.4 | −20.2 |
| " 6 | −3.5 | −1.5 | 0 | −0.5 | 0 | −1.8 | +0.8 | −3.5 |
| " 7 | −1.3 | +2.1 | −1.0 | 0 | −0.2 | −1.9 | +2.3 | +3.4 |
| " 8 | +3.0 | −0.2 | +1.3 | −0.5 | +0.4 | −0.1 | +2.9 | −7.8 |

The use of the present apparatus using the above-mentioned annular feeding device always permits the formation of a uniform thin film of organic liquid on the reaction surface, so that the resulting product is non-coloured and little accompanied by the formation of by-products, and thus a high quality of sulfonated product is obtained. Unlike the conventional apparatus using a feeding device such as a net, the present apparatus has the slots free from clogging of minute dusts or impurities contained in the organic liquid and therefore can be subject to a long, stable continuous operation.

The present apparatus for continuous sulfonation is mainly suitable to the production of a surface-active agent and is further suitable to the sulfonation for production of ordinary dyes or medicines.

The uniformity of the thin film of organic liquid formed on the reaction surface was measured by the following experiments:

The uniformity of thin films of organic liquid formed on the reaction surfaces by using the present apparatus provided with the annular feeding devices and the conventional apparatus provided with a slit opening, respectively, were determined by measurement of flow quantity. Measurement was made at a respective one of As seen from Table 1, the conventional apparatus provided with a slit opening indicated a large variation in the flow quantity on the reaction surface, whereas the present apparatus provided with the annular feeding devices each having a slot area of 40 to 90% indicated a very uniform quantity of flow, whereby an excellent quality of sulfonated product was obtained.

EXAMPLE 1

By the use of the present apparatus for continuous sulfonation provided with the annular feeding devices, the α-olefin having 16 to 18 carbon atoms (having an average molecular weight of 235) was sulfonated by SO₃ gas. For comparison, a similar test was carried out by using the conventional apparatus provided with a slit-like opening. Both tests were performed under the condition wherein the length of reaction wall was 2m; the amount of α-olefin fed was 250 kg/m.hr.; the molar ratio of SO₃ to α-olefin was 1.14; the temperature of cooling water of water-cooling jacket was 20° C; and the temperature of sulfonation reaction was 55° C to 60° C. The results from the above-sulfonated products are presented in Table 2.

Table 2

| Annular feeding device | Apparatus for continuous sulfonation provided with annular feeding devices | | | | | | Prior art |
|---|---|---|---|---|---|---|---|
| a (mm) | 0.4 | 0.4 | 0.4 | 0.4 | 0.4 | 0.4 | 0.3 |

Table 2-continued

| Annular feeding device | Apparatus for continuous sulfonation provided with annular feeding devices | | | | | | Prior art |
|---|---|---|---|---|---|---|---|
| b (mm) | 3 | 3 | 3 | 3 | 3 | 3 | (slit) |
| Percentage of slot area (%) | 40 | 50 | 67 | 80 | 90 | 95 | 100 |
| Quality of sulfonated product | | | | | | | |
| Content of unreacted oil (wt %)*1 | 2.70 | 2.68 | 2.71 | 2.72 | 2.70 | 2.75 | 2.9 |
| colouring *2 | 0.125 | 0.115 | 0.110 | 0.110 | 0.120 | 0.150 | 0.205 |
| Content of disulfonate *3 | 8.0 | 8.1 | 7.5 | 7.9 | 8.0 | 8.5 | 10.1 |

Note:
*1 Petroleum ether extract (active basis) (Hereinafter the same as this)
*2 25% concentration, absorbance (or light absorption), 10mm Cell, 420 mμ (Hereinafter the same as this)
*3 Weight % of disulfonate contained in the surface-active agent (Hereinafter, the same as this)

As apparent from Table 2, the surface-active agent produced by the present apparatus is mush less coloured than that produced by the conventional apparatus, and is not excessively sulfonated to be of a very excellent quality.

EXAMPLE 2

By the use of the present apparatus provided with the annular feeding devices of Example 1 having a slot area of 67%, sulfonation was carried out, using a aliphatic alcohol having 12 carbon atoms (having a molecular weight of 204) as the organic liquid to be sulfonated, in the same manner as in Example 1 except for the following conditions:

| | |
|---|---|
| Molar ratio of $SO_3$ | 1.03 |
| Amount of aliphatic alcohol fed | 250 kg/m. hr |
| Amount of diluting air | 3 Nm³/min. |
| Temperature of cooling water | 25° C |

The results being presented in Table 3, together for comparison with the results obtained with the same conventional apparatus having a slit-like opening as used in Example 1.

Table 3

| Quality of surface-active agent | This invention | Prior art |
|---|---|---|
| Content of unreacted oil (wt %) | 2.80 | 2.95 |
| Colouring (10% aqueous solution) | 0.11 | 0.19 |
| Inorganic salt (wt %)*4 | 0.45 | 0.56 |

Table 3 shows that the present apparatus for continuous sulfonation is very excellent as compared with the conventional apparatus.

EXAMPLE 3

By the use of the present apparatus provided with the annular feeding devices having an $a$ of 0.6 mm, a $b$ of 4 mm, and a slot area of 67 %, sulfonation was carried out using as the organic liquid to be sulfonated an alcohol ethoxylate added with 3 mole of ethylene oxide (a molecular weight of 330) in the same manner as in Example 1 except for the following conditions:

| | |
|---|---|
| Molar ratio of $SO_3$ | 1.03 |
| Amount of alcohol ethoxylate fed | 300 kg/m.hr |
| Amount of diluting air | 3 Nm³/min. |
| Temperature of cooling water | 25° C |

For comparison, by the use of the conventional apparatus provided with a slit opening the vertical clearance $a$ of which is 0.4 mm, a similar experiment was made, the results being shown in Table 4 together with the results obtained with the above present apparatus.

Table 4

| Quality of surface-active agent | This invention | Prior art |
|---|---|---|
| Content of unreacted oil (wt %) *5 | 2.10 | 2.15 |
| Colouring (10% aqueous solution) | 0.010 | 0.020 |
| Inorganic salt (wt %) | 0.30 | 0.32 |

Note:
*5 ion-exchange resin method

EXAMPLE 4

Sulfonation was carried out in the same manner as in Example 2 except for the use of an alkylbenzene (having a molecular weight of 243) as the organic liquid to be sulfonated and the following conditions. The conventional apparatus used for comparison was the same as that used in Example 2.

| | |
|---|---|
| Molar ratio of $SO_3$ | 1.05 |
| Amount of alkylbenzene feed | 300 kg/m.hr |
| Amount of diluting air | 3 Nm³/min. |
| Temperature of cooling water | 20° C |

The results in both cases are indicated in Table 5 below.

Table 5

| Quality of surface-active agent | This invention | Prior art |
|---|---|---|
| Content of unreacted petroleum oil (wt %) | 1.30 | 1.35 |
| Colouring (10% aqueous solution) | 0.010 | 0.015 |
| Inorganic salt (wt %) | 1.25 | 1.20 |

What is claim is:

1. In an apparatus for continuous sulfonation comprising at least one vertically extending, cylindrical reaction wall having a reaction surface down which a liquid material to be sulfonated flows in the form of a thin film, and at least one annular nozzle for feeding a gaseous sulfonating agent to a corresponding reaction zone, wherein the improvement comprises an annular feeding device mounted on an upper end of said at least one cylindrical reaction wall for feeding said liquid material to be sulfonated to said reaction surface, and having a number of rectangular slots horizontally equidistantly arranged in a row; and in the percentage of slot area expressed by the formula:

$$\frac{a \times c}{a(b+c)} \times 100$$

where $a$ represents the vertical clearance of the opening of each slot and is in the range of 0.2 mm to 1.0 mm; $b$ the interval between two adjacent slots; and $c$ the horizontal width of opening of each slot; said $a$, $b$ and $c$ are so chosen as to permit said percentage of slot area to range from 40 to 90%.

2. An apparatus according to claim 1, characterized in that said percentage of slot area is in the range of 50% to 90%.

3. An apparatus according to claim 1, characterized in that said $b$ is in the range of 1 mm to 5 mm.

4. An apparatus according to claim 1 characterized in that said annular nozzle is opened slightly below said annular feeding device so as to feed a gaseous sulfonating agent in parallel-flow relation to thin film of said liquid material.

5. An apparatus according to claim 1, characterized in that said cylindrical reaction wall is provided with a cooling jacket for removing the reaction heat.

6. An apparatus according to claim 1, characterized in that two externally cooled cylindrical reaction walls are so longitudinally concentrically provided that their respective reaction surfaces are opposed to each other; an inner annular feeding device for permitting a liquid material fed to a circular chamber defined inside said device to flow through the slots in the form of a thin film down a reaction surface of a inner reaction wall is provided at an upper end of said inner reaction wall and an outer annular feeding device for permitting a liquid material fed to a circular chamber defined outside said device to flow through the slots in the form of a thin film down a reaction surface of an outer reaction wall is provided at an upper end of said outer reaction wall; and an annular nozzle for feeding a gaseous sulfonating agent to a reaction zone defined by said two reaction surfaces in parallel-flow relation to the thin film of said liquid material is opened slightly below said annular feeding devices.

* * * * *